US009457194B2

(12) United States Patent
Boogaard

(10) Patent No.: US 9,457,194 B2
(45) Date of Patent: Oct. 4, 2016

(54) METHOD FOR FABRICATING AN IMPLANTABLE LEAD FOR APPLYING ELECTRICAL PULSES TO TISSUE OF A PATIENT AND SYSTEM FOR FABRICATION THEREOF

(75) Inventor: Jerome Boogaard, Forest Grove, OR (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 1142 days.

(21) Appl. No.: 13/401,633

(22) Filed: Feb. 21, 2012

(65) Prior Publication Data

US 2012/0215339 A1 Aug. 23, 2012

Related U.S. Application Data

(60) Provisional application No. 61/444,891, filed on Feb. 21, 2011.

(51) Int. Cl.
A61N 1/375 (2006.01)
A61N 1/39 (2006.01)
A61N 1/05 (2006.01)

(52) U.S. Cl.
CPC ............ A61N 1/375 (2013.01); A61N 1/0563 (2013.01); A61N 1/3962 (2013.01)

(58) Field of Classification Search
None
See application file for complete search history.

(56) References Cited

U.S. PATENT DOCUMENTS 4,534,002 A * 8/1985 Urban .......................... 700/171
5,580,699 A    12/1996 Layman et al.
8,184,301 B2 * 5/2012 Benz et al. ................... 356/614
2002/0104750 A1 * 8/2002 Ito .............................. 204/157.15
2007/0228023 A1 * 10/2007 Kleine et al. ............ 219/121.67
2008/0088856 A1 * 4/2008 Nishio ......................... 356/623
2008/0170891 A1 * 7/2008 Abe et al. .................... 399/277
2010/0137928 A1    6/2010 Duncan
2010/0204767 A1 * 8/2010 Zhao ........................... 607/122
2010/0329760 A1 * 12/2010 Nishida et al. .............. 399/396
2011/0112402 A1 * 5/2011 Yokota et al. ............... 600/443
2012/0130218 A1 * 5/2012 Kauphusman et al. ...... 600/373

FOREIGN PATENT DOCUMENTS

WO    WO/2009/081599    *    7/2009    ............... A61B 8/08

OTHER PUBLICATIONS

European Patent Office, International Search Report and Written Opinion dated Jun. 12, 2012 for PCT/US2012/025961.

* cited by examiner

Primary Examiner — Mohammad Ali
Assistant Examiner — Saad M Kabir

(57) ABSTRACT

In one embodiment, a method of fabrication an implantable lead for providing electrical pulses to tissue of a patient, the method comprises: (i) providing a sheath of transparent insulative material, wherein the sheath comprises a plurality of lumens; (ii) scanning across the sheath with a confocal displacement meter to generate displacement data; (iii) processing the displacement data, in software executed on a computer system, to generate a representation of an exterior surface and lumens of the sheath; (iv) automatically selecting locations, in software executed on a computer system, on the exterior surface of application of laser pulses to create apertures in the sheath that provide access to respective lumens of the sheath; and (v) applying laser pulses according to the sheath to create the apertures.

12 Claims, 8 Drawing Sheets

METHOD FOR FABRICATING AN IMPLANTABLE LEAD FOR APPLYING ELECTRICAL PULSES TO TISSUE OF A PATIENT AND SYSTEM FOR FABRICATION THEREOF

CROSS-REFERENCE TO RELATED APPLICATIONS

This application claims the benefit of U.S. Provisional Application No. 61/444,891, filed Feb. 21, 2011, which is incorporated herein by reference.

TECHNICAL FIELD

This application is generally related to fabricating an implantable lead by employing confocal displacement optical imaging to control laser ablation operations.

BACKGROUND

Implantable cardiac therapy devices (ICTDs) enjoy widespread use for providing convenient, portable, sustained therapy for cardiac patients with a variety of cardiac arrhythmias. ICTDs may combine a pacemaker and defibrillator in a single implantable device. Such devices may be configured to provide ongoing cardiac pacing in order to maintain an appropriate cardiac rhythm. In addition, should the ICTD detect that the patient is experiencing an episode of ventricular fibrillation (or an episode of ventricular tachycardia), the ICTD can deliver appropriate defibrillation therapy.

Cardiac rhythm management (CRM) therapies require not only an ICTD, but also the placement of electrical leads threaded through blood vessels and typically into the heart itself. Patients with implanted electrical leads benefit from leads which exhibit optimized properties in terms of size (that is, minimal lead width or diameter), flexibility, strength, and reliability (including resistance to breaking), and various electrical properties such as low impedance (in order to carry large current loads).

With advances in both CRM therapy and ICTD technologies, the device implant pathway can become busy with three or more cables (for example, cables may be required for treating bradycardia, tachycardia, defibrillation, cardiac pacing, for standalone sensors, etc.). These multiple leads may need to be placed inside only one or two veins, which in turn benefit from smaller size leads to ensure adequate circulation through the blood vessels. Adding new sensor based diagnostic features, such as LAP (left atrial pressure), RVP (right ventricular pressure), and $SvO_2$ (blood oxygen sensor), requires creating additional space in the implant pathway or the lead body for the diagnostic circuits. Therefore, the addition of such sensors requires that the regular ICD lead diameter again must be reduced. Potential target drug delivery and target biological therapy delivery of tissues, cells, antibodies genes, etc. needs to be specifically delivered via a lead channel in the given vein with the new ICD leads. All of these therapeutic demands create requirements for the thinnest possible leads consistent with other lead requirements (flexibility, durability, low electrical resistance, and others).

With recent advances in cardiac therapies, alternative ICD lead implant sites are increasingly used. These include: the right ventricular outflow tract (ROT), the right ventricular (RV) high septum, and other sites in the right heart; and also the cardiac septum (CS), the great cardiac vein, and other areas of the left heart. To this end, the ICD leads must be robust and flexible for site specific positioning, and for ease of implantation through the torturous and complex implant pathways. ICTD leads also require improved acute and chronic stability at the desired site to reliably deliver the desired therapies for the entire design life of the system.

The various operational requirements for ICTD leads, create competing design requirements. In general, thinner leads contribute to flexibility and allow for maximum circulation within blood vessels. However, thinner leads present other technical complexities including fabrication difficulties and expense.

It will be noted that while implantable leads are essential in the field of cardiac rhythm management (CRM) therapies, implantable leads are employed in many other biomedical applications as well. For example, implantable leads have applications in neurology for treatment of Parkinson's disease, epilepsy, chronic pain, and other many other conditions. Many of the requirements identified above, such as small size (i.e., being as thin as possible), flexibility, durability, and low resistance are important for these other applications as well.

SUMMARY

In one embodiment, a method of fabrication an implantable lead for providing electrical pulses to tissue of a patient, the method comprises: (i) providing a sheath of transparent insulative material, wherein the sheath comprises a plurality of lumens; (ii) scanning across the sheath with a confocal displacement meter to generate displacement data; (iii) processing the displacement data, in software executed on a computer system, to generate a representation of an exterior surface and lumens of the sheath; (iv) automatically selecting locations, in software executed on a computer system, on the exterior surface for application of laser pulses to create apertures in the sheath that provide access to respective lumens of the sheath; and (v) applying laser pulses according to the sheath to create the apertures.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Before describing in detail the methods and systems for fabricating implantable leads, it is helpful to describe an example environment. The methods and systems described herein may be particularly useful for implantable leads for use in the environment of an implantable cardiac therapy device (ICTD).

An ICTD is a physiologic measuring device and therapeutic device that is implanted in a patient to monitor cardiac function and to deliver appropriate electrical therapy, for example, pacing pulses, cardioverting and defibrillator pulses, and drug therapy, as required. ICTDs include, for example and without limitation, pacemakers, cardioverters, defibrillators, implantable cardioverter defibrillators, implantable cardiac rhythm management devices, and the like. Such devices may also be used in particular to monitor cardiac electrical activity and to analyze cardiac electrical activity. The term "implantable cardiac therapy device" or simply "ICTD" is used herein to refer to any such implantable cardiac device.

The techniques described below are intended to be implemented in connection with any ICTD or any similar stimulation device that is configured or configurable to stimulate nerves throughout a patient's body and/or stimulate and/or shock a patient's heart.

Figure 1:
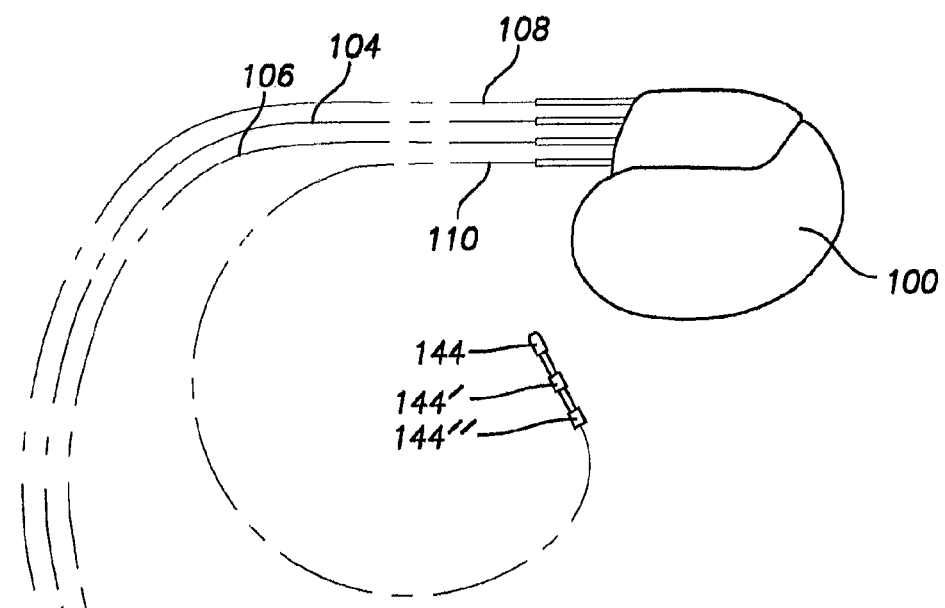
FIG. 1 depicts an exemplary stimulation device in electrical communication with a patient's heart by way of three leads, suitable for delivering multi-chamber stimulation and shock therapy.
Figure 1:
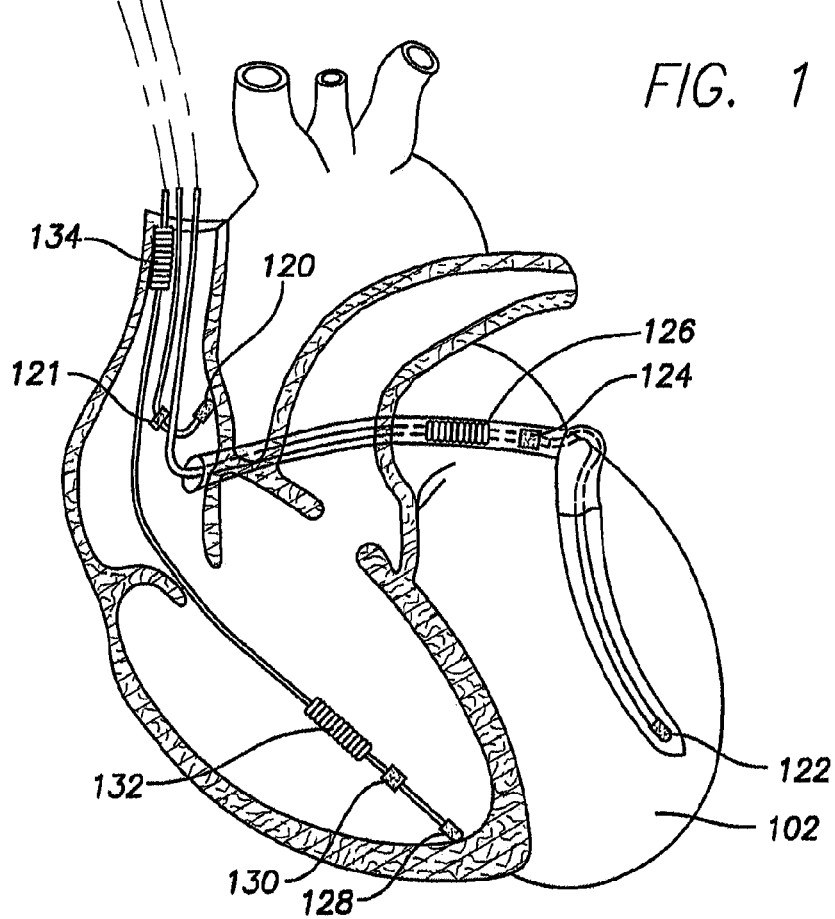

FIG. 1 shows an exemplary stimulation device 100 in electrical communication with a patient's heart 102 by way of three leads 104, 106, 108, suitable for delivering multichamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue. Exemplary leads 104, 106, 108, 110 have at least one interior electrically conducting cable (alternatively referred to as a conductor wire), and may have multiple interior electrically conducting cables.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and a superior vena cava (SVC) coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

An implantable cardiac therapy device may be referred to variously, and equivalently, throughout this document as an "implantable cardiac therapy device", an "ICTD", an "implantable device", a "stimulation device", and the respective plurals thereof.

Figure 2:
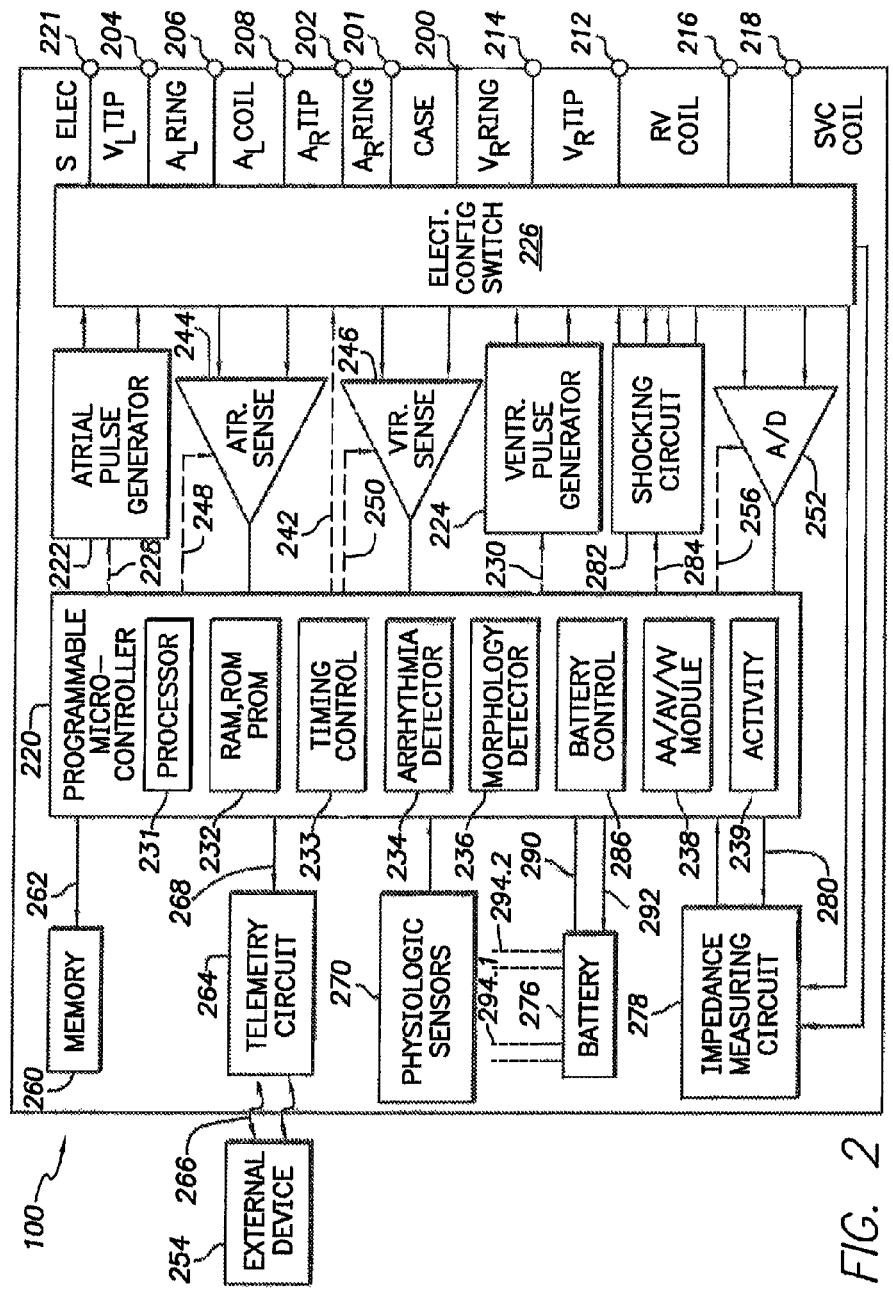
FIG. 2 depicts an exemplary, simplified block diagram depicting various components of stimulation device of FIG. 1.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132, and 134 (see FIG. 1) for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal (AR TIP) 202 adapted for connection to the atrial tip electrode 120. A right atrial ring terminal (AR RING) 201 is also shown, which is adapted for connection to the atrial ring electrode 121. To achieve left chamber sensing, pacing, shocking, and/or autonomic stimulation, the connector includes at least a left ventricular tip terminal (VL TIP) 204, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a processor or microprocessor 231, or equivalent control circuitry, designed specifically for controlling the delivery of stimulation therapy, and may further include onboard memory 232 (which may be, for example and without limitation, RAM, ROM, PROM, one or more internal registers, etc.), logic and timing circuitry, state machine circuitry, and I/O circuitry.

Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 233 to control the timing of the stimulation pulses (e.g., pacing rate, atrio-ventricular (e.g., AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module (the latter two are not shown in FIG. 2). These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, bi-ventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays. Such a module may help make determinations as to fusion.

The microcontroller 220 of FIG. 2 also includes an activity module 239. This module may include control logic for one or more activity related features. For example, the module 239 may include an algorithm for determining patient activity level, calling for an activity test, calling for a change in one or more pacing parameters, etc. The module 239 may be implemented in hardware as part of the microcontroller 220, or as software/firmware instructions programmed into the device and executed on the microcontroller 220 during certain modes of operation. The module 239 may act cooperatively with the AA/AV/VV module 238.

Microcontroller 220 may also include a battery control module 286. Battery control module 286 may be used, for example, to control a battery 276. Battery control 286 may be hardwired circuitry, or may be implemented as software or firmware running on microcontroller 220. Battery control 286 may be coupled to battery 276 via battery signal line 290 and battery control line 292. Battery signal line 290 may deliver to battery control 286 status or operational information regarding battery 276. Battery control line 292 may be used to change an operational state of battery 276. For example, battery control line 292 may deliver control signals from battery control 286 to battery 276.

In an alternative embodiment, battery control 286 may be a separate module from microcontroller 220, but may be coupled to microcontroller 220. For example, separate module battery control 286 may obtain required ICTD operational status information from microcontroller 220. Or, for example, separate module battery control 286 may report battery status or battery operational information to microcontroller 220. In addition, separate module battery control 286 may also be coupled to battery 276.

In an alternative embodiment, battery control 286 may be implemented as an internal physical module of battery 276 (for example, battery control 286 may be implemented as a microchip which is situated internally to the exterior housing of battery 276). However, battery control 286 may still be coupled to microcontroller 220 via battery signal line 290 and battery control line 292. In an alternative embodiment, battery control functions of battery control 286 may be distributed across a first module which is part of battery 276, and one or more additional modules which are external to battery 276. The battery control module(s) external to battery 276 may for example be part of microcontroller 220.

The electrode configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR.SENSE) and ventricular (VTR.SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the analog-to-digital (A/D) data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram (EGM) signals, convert the raw analog data into a digital signal, and store the digital signals for later processing and/or telemetric transmission to an external device 254. Data acquisition system 252 may be configured by microcontroller 220 via control signals 256. The data acquisition system 252 is coupled to the right atrial lead 104, the coronary sinus lead 106, the right ventricular lead 108 and/or the nerve stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature may be the ability to sense and store a relatively large amount of data (e.g., from the data acquisition system 252), which data may then be used for subsequent analysis to guide the programming of the device.

Essentially, the operation of the ICTD control circuitry, including but not limited to pulse generators, timing control circuitry, delay modules, the activity module, battery utilization and related voltage and current control, and sensing and detection circuits, may be controlled, partly controlled, or fine-tuned by a variety of parameters, such as those indicated above which may be stored and modified, and may be set via an external ICTD programming device.

Advantageously, the operating parameters of the implantable device 100 may be non-invasively programmed into the memory 260 through a telemetry circuit 264 in telemetric communication via communication link 266 with the external device 254, such as a general purpose computer, a dedicated ICTD programmer, a transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266. The ICTD 100 may also receive human programmer instructions via the external device 254.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 may respond by adjusting the various pacing parameters (such as rate, AA delay, AV delay, W delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of an example activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2, as well as to any additional circuits which may be present in alternative embodiments. Operating power in the form of electrical current and/or voltage may be provided via a power bus or power buses 294, depicted in FIG. 2 as a first power bus 294.1 and a second power bus 294.2. In FIG. 2, the connection(s) of power bus(es) 294 to other elements of ICTD 100 for purposes of powering those elements is not illustrated, but is implied by the dotted end-lines of bus(es) 294.

For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 Amps, at voltages above 2 volts, for periods of 10 seconds or more). In an embodiment, battery 276 may be configured to provide a current as high as 3.5 to 4.5 Amps and/or unloaded voltages in excess of 4 volts, for rapid charging of shocking circuitry. Battery 276 also desirably has a predictable discharge characteristic so that elective replacement time can be determined.

In an embodiment, battery 276 may be a hybrid battery comprised of dual types of cells. Such a hybrid battery may provide power via a plurality of power buses, such as buses 249.1 and 294.2 of FIG. 2. In an embodiment, each power bus may be configured to deliver different voltages, different currents, and/or different power levels. Battery 276 may be monitored and/or controlled via battery control 286, as discussed in part above, and as also discussed further below.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuit 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICTD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV coil electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Shocking circuit 282 either has within it, or is coupled to, one or more shocking capacitors (not shown in FIG. 2). The shocking capacitor(s) may be used to store up energy, and then release that energy, during the generation of shocking pulses.

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, microcontroller 220 is capable of controlling the synchronous or asynchronous delivery of the shocking pulses.

As indicated above, the operating parameters of the implantable device 100 may be non-invasively programmed into the memory 260 through a telemetry circuit 264 in telemetric communication via communication link 266 with the external device 254. The external device 254 may be a general purpose computer running custom software for programming the ICTD 100, a dedicated external programmer device of ICTD 100, a transtelephonic transceiver, or a diagnostic system analyzer. Generically, all such devices may be understood as embodying computers, computational devices, or computational systems with supporting hardware or software which enable interaction with, data reception from, and programming of ICTD 100.

Throughout this document, where a person is intended to program or monitor ICTD 100 (where such person is typically a physician or other medical professional or clinician), the person is always referred to as a "human programmer" or as a "user". The term "human programmer" may be viewed as synonymous with "a person who is a user of an ICTD programming device", or simply with a "user". Any other reference to "programmer" or similar terms, such as "ICTD programmer", "external programmer", "programming device", etc., refers specifically to the hardware, firmware, software, and/or physical communications links used to interface with and program ICTD 100.

The terms "computer program", "computer code", and "computer control logic" are generally used synonymously and interchangeably in this document to refer to the instructions or code which control the behavior of a computational system. The term "software" may be employed as well, it being understood however that the associated code may in some embodiments be implemented via firmware or hardware, rather than as software in the strict sense of the term (e.g., as computer code stored on a removable medium, or transferred via a network connection, etc.).

A "computer program product" or "computational system program product" is a medium (for example, a magnetic disk drive, magnetic tape, optical disk (e.g., CD, DVD), firmware, ROM, PROM, flash memory, a network connection to a server from which software may be downloaded, etc) which is suitable for use in a computer or computation system, or suitable for input into a computer or computational system, where the medium has control logic stored therein for causing a processor of the computational system to execute computer code or a computer program. Such medium, also referred to as "computer program medium", "computer usable medium", and "computational system usable medium", are discussed further below.

Figure 3:
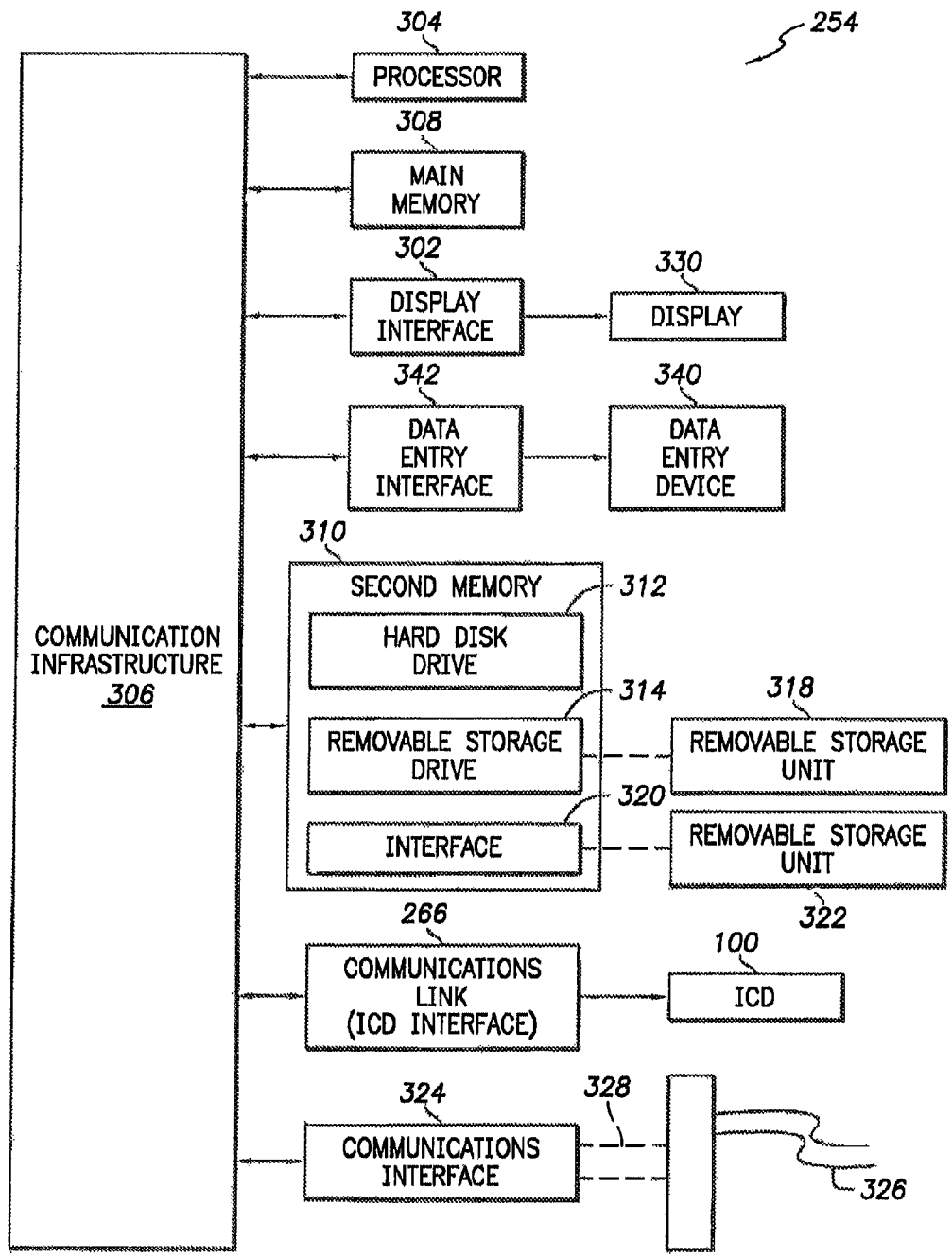
FIG. 3 depicts a system diagram of an ICTD programmer.

FIG. 3 presents a system diagram representing an exemplary computer, computational system, or other programming device, which will be referred to for convenience as ICTD programmer 254. It will be understood that while the device is referred to an "ICTD programmer", indicating that the device may send programming data, programming instructions, programming code, and/or programming parameters to ICTD 100, the ICTD programmer 254 may receive data from ICTD 100 as well, and may display the received data in a variety of formats, analyze the received data, store the received data in a variety of formats, transmit the received data to other computer systems or technologies, and perform other tasks related to operational and/or physiologic data received from ICTD 100.

ICTD programmer 254 includes one or more processors, such as processor 304. Processor 304 is used for standard computational tasks well known in the art, such as retrieving instructions from a memory, processing the instructions, receiving data from memory, performing calculations and analyses on the data in accordance with the previously indicated instructions, storing the results of calculations back to memory, programming other internal devices within ICTD programmer 254, and transmitting data to and receiving data from various external devices such as ICTD 100.

Processor 304 is connected to a communication infrastructure 306 which is typically an internal communications bus of ICTD programmer 254; however, if ICTD programmer 254 is implemented in whole or in part as a distributed system, communication infrastructure 306 may further include or may be a network connection.

ICTD programmer 254 may include a display interface 302 that forwards graphics, text, and other data from the communication infrastructure 306 (or from a frame buffer not shown) for display on a display unit 330. The display unit may be, for example, a CRT, an LCD, or some other display device. Display unit 330 may also be more generally understood as any device which may convey data to a human programmer.

Display unit 330 may also be used to present a user interface which displays internal features of, operating modes or parameters of, or data from ICTD 100. The user interface presented via display unit 330 of ICTD programmer 254 may include various options that may be selected, deselected, or otherwise changed or modified by a human programmer of ICTD 100. The options for programming the ICTD 100 may be presented to the human programmer via the user interface in the form of buttons, check boxes, menu options, dialog boxes, text entry fields, or other icons or means of visual display well known in the art.

ICTD programmer 254 may include a data entry interface 342 that accepts data entry from a human programmer via data entry devices 340. Such data entry devices 340 may include, for example and without limitation, a keyboard, a mouse, a touchpad, a touch-sensitive screen, a microphone for voice input, or other means of data entry, which the human programmer uses in conjunction with display unit 330 in a manner well known in the art. For example, either a mouse or keystrokes entered on a keyboard may be used to select check boxes, option buttons, menu items, or other display elements indicating human programmer choices for programming ICTD 100. Direct text entry may be employed as well. Data entry device 340 may also take other forms, such as a dedicated control panel with specialized buttons and/or other mechanical elements or tactile sensitive elements for programming ICTD 100.

Display interface 302 may present on display unit 330 a variety of data related to patient cardiac function and performance, and also data related to the present operating mode, operational state, or operating parameters of ICTD 100. Modifications to ICTD 100 operational state(s) may be accepted via data entry interface 342 and data entry device 340. In general, any interface means which enables a human programmer to interact with and program ICTD 100 may be employed. In one embodiment, for example, a visual data display may be combined with tactile data entry via a touch-screen display.

In another embodiment, a system of auditory output (such as a speaker or headset and suitable output port for same, not shown) may be employed to output data relayed from ICTD 100, and a system of verbal input (such as a microphone and suitable microphone port, not shown) may be employed to program ICTD 100. Other modes of input and output means may be employed as well including, for example and without limitation, a remote interaction with ICTD 100, viewing printed data which has been downloaded from ICTD 100, or the programming of ICTD 100 via a previously coded program script.

All such means of receiving data from ICTD 100 and/or programming ICTD 100 constitute an interface 302, 330, 342, 340 between ICTD 100 and a human programmer of ICTD 100, where the interface is enabled via both the input/output hardware (e.g., display screen, mouse, keyboard, touchscreen, speakers, microphone, input/output ports, etc.) and the hardware, firmware, and/or software of ICTD programmer 254.

ICTD programmer 254 also includes a main memory 308, preferably random access memory (RAM), and may also include a secondary memory 310. The secondary memory 310 may include, for example, a hard disk drive 312 and/or a removable storage drive 314. The removable storage drive 314 reads from and/or writes to a removable storage unit 318 in a well known manner. Removable storage unit 318 represents magnetic disk, magnetic tape, optical disk, etc. which is read by and written to by removable storage drive 314. As will be appreciated, the removable storage unit 318 includes a computer usable storage medium having stored therein computer software and/or data. In alternative embodiments, secondary memory 310 may include other similar devices for allowing computer programs or other instructions to be loaded into ICTD programmer 254. Such devices may include, for example, a removable storage unit 322 and an interface 320. Examples of such may include solid-state memory cards and drives.

ICTD programmer 254 also contains a communications link 266 to ICTD 100, which may be comprised in part of a dedicated port of ICTD programmer 254. From the perspective of ICTD programmer 254, communications link 266 may also be viewed as an ICTD interface. Communications link 266 enables two-way communications of data between ICTD programmer 254 and ICTD 100.

ICTD programmer 254 may also include a communications interface 324. Communications interface 324 allows software and data to be transferred between ICTD programmer 254 and other external devices (apart from ICTD 100). Examples of communications interface 324 may include a modem, a network interface (such as an Ethernet card), a communications port, a Personal Computer Memory Card International Association (PCMCIA) slot and card, a USB port, an IEEE 1394 (FireWire) port, etc. Software and data transferred via communications interface 324 are in the form of signals 328 which may be electronic, electromagnetic, optical (e.g., infrared) or other signals capable of being received by communications interface 324. These signals 328 are provided to communications interface 324 via a communications path (e.g., channel) 326. This channel 326 carries signals 328 and may be implemented using wire or cable, fiber optics, a telephone line, a cellular link, an radio frequency (RF) link, in infrared link, and other communications channels.

The terms "computer program medium", "computer usable medium", and "computational system usable medium" are used, synonymously, to generally refer to media such as removable storage drive 314, a hard disk installed in hard disk drive 312, a secondary memory interface (such as a flash memory port, USB port, FireWire port, etc.) and removable storage unit 322 (such as flash memory), and removable storage units 318 and 322. These computer program products or computational system program products provide software to ICTD programmer 254.

It should be noted, however, that it is not necessarily the case that the necessary software, computer code, or computer program (any of which may also referred to as computer control logic) be loaded into ICTD programmer 254 via a removable storage medium. Such computer program may be loaded into ICTD programmer 254 via communications link 328, or may be stored in memory 308 of ICTD programmer 254. Computer programs are stored in main memory 308 and/or secondary memory 310. Computer programs may also be received via communications interface 324.

Accordingly, such computer programs represent controllers of ICTD programmer 254, and thereby controllers of ICTD 100. Software may be stored in a computer program product and loaded into ICTD programmer 254 using removable storage drive 314, hard drive 312, secondary memory interface 320, or communications interface 324.

An implantable lead refers to an elongated, flexible tubular element, commonly though not necessarily with a circular cross-section orthogonal to the axis of elongation. A lead is composed of one or more cables, and a sheath which houses the cables, as defined further below. A lead has a proximal end and a distal end. The proximal end of the lead is designed to attach to a pulse generator (e.g., an ICTD or other therapeutic or sensing device). Depending upon the specific medical therapy, the distal end of the lead may be designed to have one or more elements for attaching the lead to organic tissue (e.g., fixing tines), and/or electrode elements for delivery of electricity to organic tissue (typically for therapeutic purposes), and/or other elements for delivery of other therapeutic treatments to organic tissue, and/or elements for sensing an activity of organic tissue.

In some cases, the attaching element(s) may be the same as the electrode(s), other therapeutic delivery element(s), or sensing element(s). In some cases, elements for attaching to organic tissue, for delivery of electricity, for delivery of other therapeutic treatments, or for sensing may also be placed at one or more points intermediate between the proximal end and the distal end. Suitable alterations, such as placement of punctures or holes, made be made to the sheath (defined below) and to other jacketing, coating, or insulation (defined below) to enable suitable mechanical and/or electrical connectivity between these intermediate elements and the interior electrically conducting cables and/or other interior therapeutic delivery pathways of the lead as will be discussed herein.

The body or sheath of an implantable lead is a typically non-conducting element of a lead which provides the exterior insulation of the lead and may also provide interior separation and/or insulation between two or more conducting cables (as defined below) if multiple cables are employed within the lead. The sheath typically extends the full length or almost the full length of the lead, possibly excluding the length of the proximal and distal end elements (for attaching to the pulse generator or ICTD, electrodes, etc.). As will be understood by persons skilled in the relevant arts, the sheath of a lead may have multiple layers, for example an inner insulating sheath and an outermost sheath. The sheath may be made from any number of materials which demonstrate resilience and flexibility including, for example and without limitation, silicone rubber, polyurethane, Optim® (a silicone-polyurethane co-polymer insulation), PTFE (polytetrafluoroethylene), or ETFE (ethylene-tetrafluoroethylene), polyimide, paryline, PFA, etc.

In some lead designs, the sheath provides one or more hollow, mutually insulated interior canals or tubular spaces known as "lumens," running substantially parallel to the outer wall of the sheath, which typically run the full length or substantially the full length of the sheath. The lumens are designed to provide a pathway for one or more electrically conducting cables and/or coil conductors for delivery of therapeutic treatments or for sensing, or pathways for delivery of other therapeutic treatments. One or more lumens may also be designed to accommodate a stylet or wire guide, etc. When a sheath has two or more lumens running through it, these may be referred to together as a multilumen. In this document, the term "lumen" may sometimes be used in place of "multilumen" where the context makes clear the meaning, or where either a lumen (single canal) or multilumen may be intended.

A cable is an electrically conducting element made from a conducting material (including for example and without limitation silver, copper, nickel, chromium, aluminum, iron, molybdenum, etc., and/or various alloys of these metals and other metals), typically running the full length or substantially the full length of an ICTD or other medical lead. The conducting elements of a cable (central core, cable-layers, and filaments, defined further below) are also composed of conducting elements (including for example and without limitation silver, copper, nickel, chromium, aluminum, iron, molybdenum, etc., and/or various alloys of these metals and other metals). A cable may also have within it non-conducting materials and/or coatings, as discussed further below.

For ICTD leads, a cable is typically dedicated to, and designed for, carrying a single type of electrical signal or therapeutic electricity. For example, a cable may be dedicated to right ventricular (RV) shocking, or to superior vena cava (SVC) shocking, or to sensing cardiac activity. In some cases, a cable may be configured for dual purposes (for example, shocking and sensing), but will typically still be configured to carry only a single electrical signal at a time (for example, either a shocking charge or a sensing signal). Functionally, a cable is equivalent to what may be conventionally viewed as a single conductor or single wire carrying electricity. However, a cable may actually be comprised of multiple filaments of electrically conductive material. At the proximal end, the cable may include means for connection with the pulse generator (e.g., a ICTD) or other therapeutic device, and at the distal end may be an electrode or other element for delivery of therapeutic treatment or for sensing purposes. Other elements may be attached between the proximal and distal ends, connected to the cable via holes in the lumen.

Figure 4A:
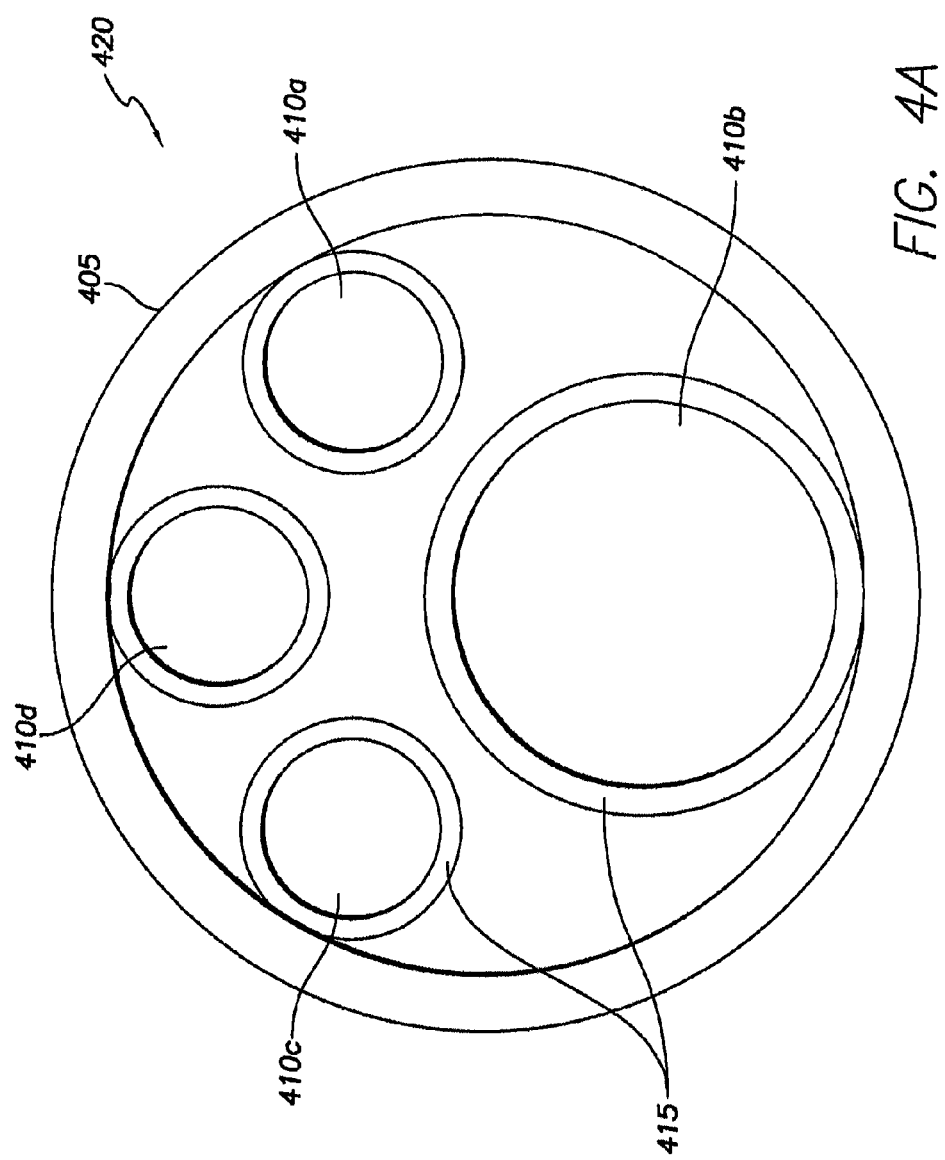
FIGS. 4A and 4B depict a sheath design including four lumens that may be processed according to some representative embodiments.

FIG. 4A illustrates in cross-section another exemplary implantable ICTD lead 420 according to one representative embodiment. In this embodiment, lead 420 comprises one generally central lumen and three lumens on the periphery of lead 420, where: lumen 410a is configured for SVC shocking; lumen 410b is configured for a pacing coil with stylet; lumen 410c is configured for RV shocking; and lumen 410d is configured for a sensing cable. Lumen 410a and lumen 410b are designed to hold single cables. In addition as shown in the embodiment of FIG. 4a, all four lumens 410 may have liners 415. Notable in FIG. 4A is that lumens 410a and 410c configured to receive cables for cardiac shocking are configured to receive only a single cable. Windows are created in sheath 405 from the exterior surface of sheath 405 to lumens 410a, 410c, and 410d for electrical connection to electrodes and a sensor, respectively. Also, in one representative embodiment, the coil for lumen 410b is connected to an electrode through the distal end of sheath 405.

Figure 4B:
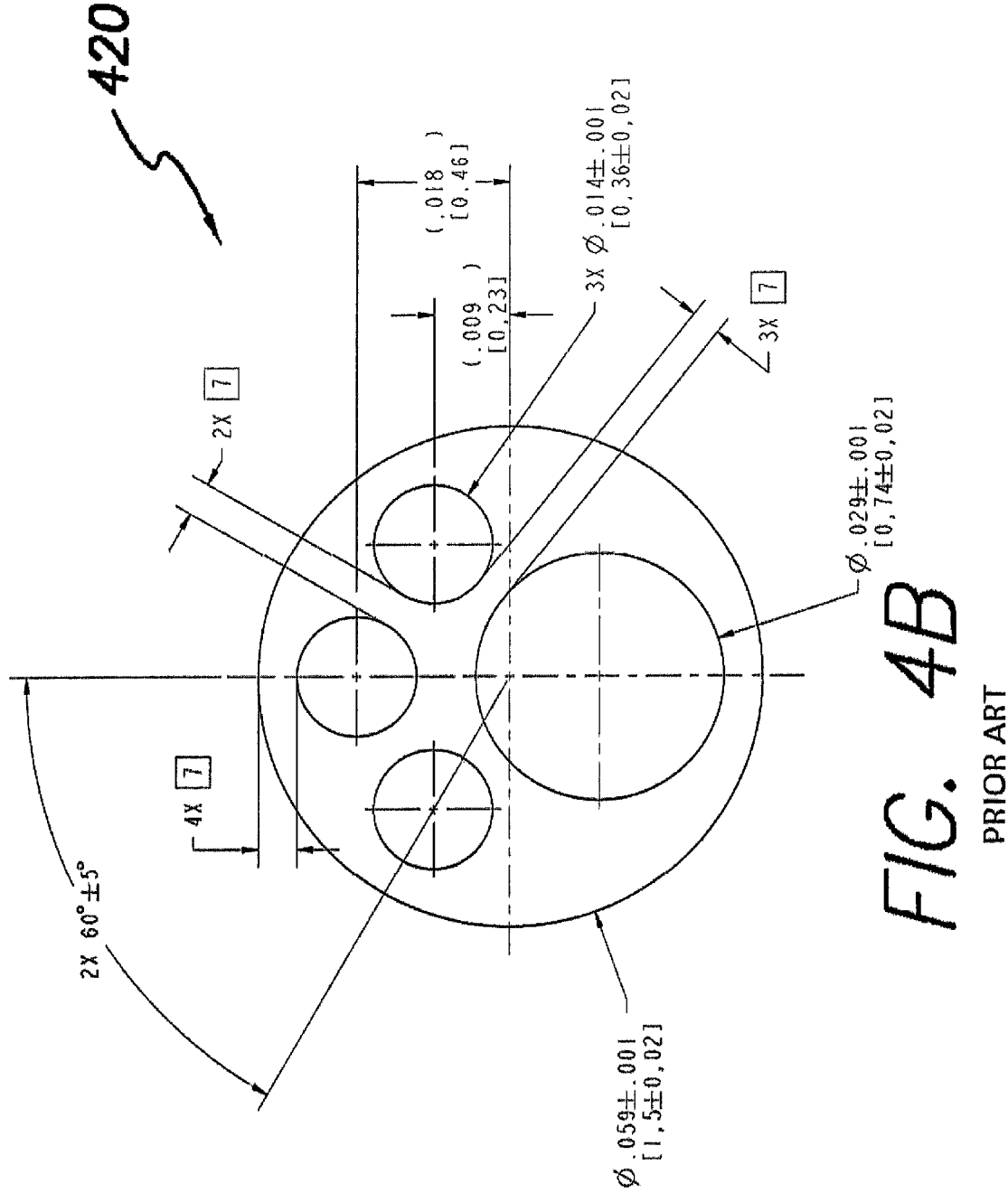

FIG. 4B is another cross-sectional view of the exemplary lead 420 shown in FIG. 4A. FIG. 4B displays exemplary measurements of the various elements such as sheath 405, lumens 410, and liners 415. The measurements are provided by way of example and are not considered part of the invention. Any dimensions may be selected that are suitable for implantable leads (cardiac leads or neurostimulation leads).

Persons skilled in the relevant arts will appreciate that the views of exemplary leads shown in FIGS. 4A-4B represent cross-sectional views only. Orthogonal to the cross-sectional views shown are the lengths of the leads, which are elongated flexible tubular elements, wherein the lumens are configured to receive such elements as cables, coils, or stylets. Cables and coils are used for such purposes as conducting electrical signals or electrical impulses for cardiac sensing and cardiac shocking Although a specific lumen configuration is shown in FIGS. 4A-4B, any suitable lumen configuration may be employed. For example, certain commercially available cardiac leads employ a five-lumen sheath design with varying shapes for selected lumens. Also, certain commercially available neurostimulation leads employ larger numbers of lumens with the sheaths. Any such sheath designs may be employed according to some embodiments.

Fabrication of implantable leads can be a challenging task. Attachment of electrodes to the lead body and coupling of the electrodes to the cables or conductors of the lead body typically involves complex, delicate operations. Frequently, holes, windows, or apertures are created in the insulative material of the sheath of the lead body. The electrodes are electrically coupled to the lead cables/conductors through these items. A variety of techniques have been employed to create the holes through the sheath. When creating the holes in the sheath, a significant amount of accuracy is important. Specifically, the removal of insulative material to access a specific lumen should not also inadvertently create access through the same hole to another lumen. Also, the removal of insulative material should not weaken the sheath beyond a point where subsequent lead processing will be unsuccessful. For example, if a lumen is too close to the outer surface of the sheath at a given axial location along the sheath, the creation of an aperture at that axial location may cause the sheath to subsequently fail during further processing or at a later time.

Known techniques to identify lumens include simple visual inspection by a system operator through a camera of a micromaching laser system. Such visual identification of the lumens by a system operator can be impractical for performance in a repeatable, reliable manner if the optical characteristics of the insulative material of the sheath cause internal reflections between the lumens of the sheath. Another technique includes inserting wires of respective colors within the lumens to increase the visibility of the lumens for identification through a processing system camera. Also, it is known to insert a fixture of multiple pins into the lumens at a distal and/or proximal end to align a given sheath and to control rotation of the sheath during insulative removal operations. However, these known techniques are not practical for all sheath designs. Smaller sheath sizes with flexible sheath materials may make the insertion of wires of respective colors into the lumens impractical and/or unduly expensive. Further, the degree of axial twist of a sheath may cause the use of a fixture for insertion into the lumens to be of limited or no benefit.

Some embodiments are directed to a system that automatically identifies the lumens of a sheath using optical imaging and processing techniques (to be discussed below). Upon identification, the system creates holes or apertures in the sheath, preferably using laser ablation.

Figure 5A:
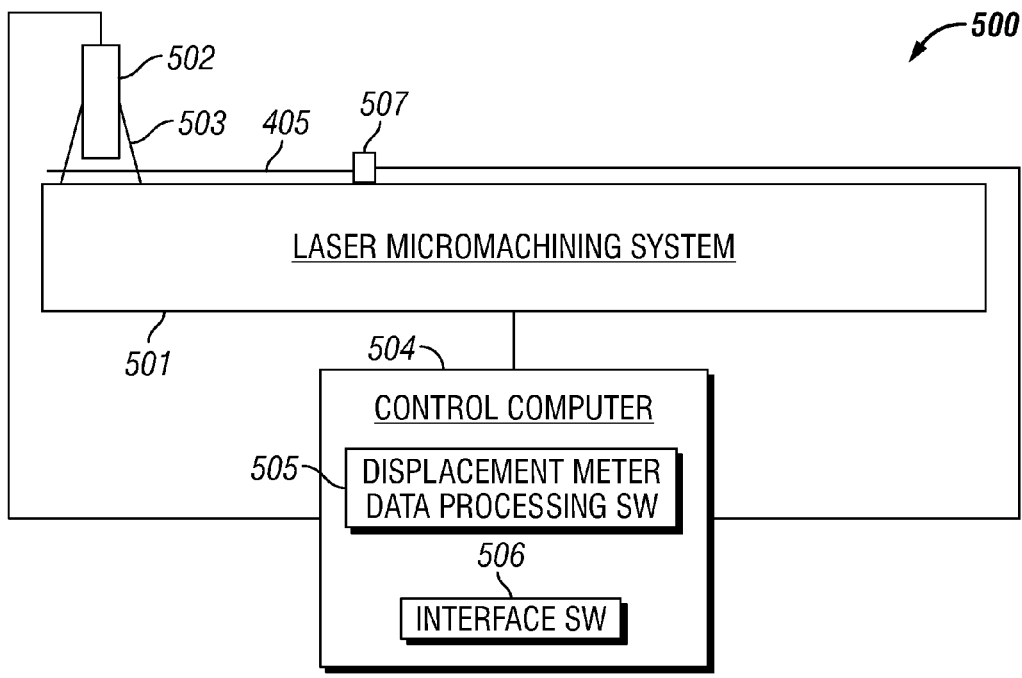
FIG. 5A depicts a block diagram of system for creating apertures or holes in sheath during fabrication of an implantable lead according to some representative embodiments.
Figure 5B:
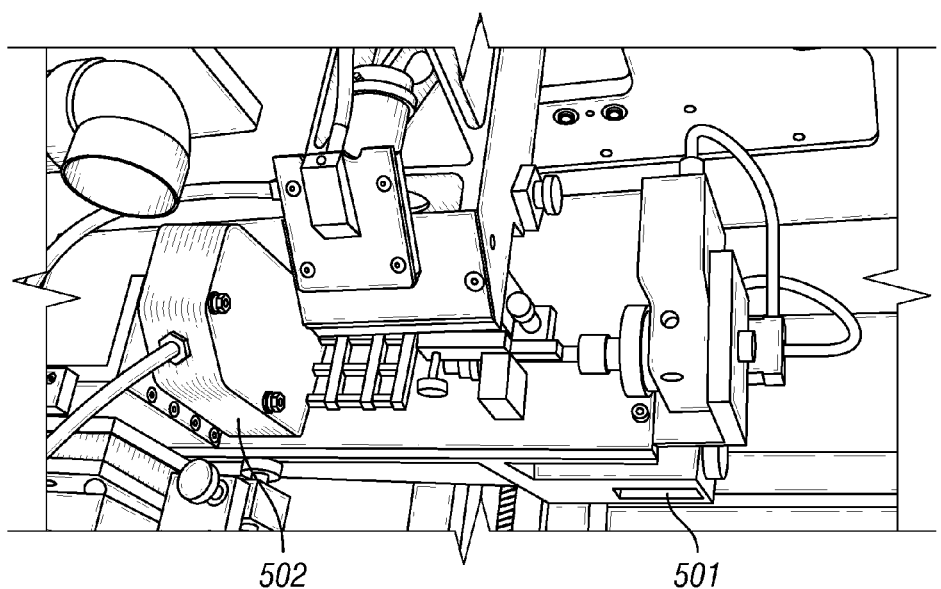
FIG. 5B depicts an image of one implementation of the system shown in FIG. 5A.

FIG. 5A depicts a block diagram of system 500 for creating apertures in a sheath for an implantable lead according to one representative embodiment. System 500 includes laser micromachining system 501. Laser system 501 may include respective components blocks such as an Nd:YAG laser, beam delivery optics, motion control components, and a frame structure (not individually depicted in FIG. 5). In some embodiments, the laser system 501 uses the $4^{th}$ harmonic of a solid state laser, e.g., a Nd:YAG, Nd:YLF laser. In other embodiments, ultra-short pulse lasers (that generate pico-second and femto-second laser pulses in both the IR and visible wavelengths) may be employed to obtain further improved micro-machining control and resolution. Laser confocal displacement meter 502 is attached to laser system 501 using fixture 503. System 500 further includes lead translation and rotation hardware 507 for rotation and axial translation within the field of use of laser system 501 and within the scanning field of displacement meter 502. Fixture 503 permits measurement data from displacement meter 502 to be correlated to a specific axial and angular position on sheath 405 for control of subsequent operation of laser system 501. FIG. 5B depicts a digital image of one implementation of system 500 including laser system 501 and laser confocal displacement meter 502. For the implementation shown in FIG. 5B, a suitable laser system 501 is available from Photonics Industries, 390 Central Ave., Bohemia, N.Y. 11716. Also, in this implementation, the laser confocal displacement meter 502 is the LT-9000 series device available from Keyence Corporation (Woodcliff Lake, N.J.). Any suitable commercial devices or custom devices may be employed for laser system 501 and confocal displacement meter 502.

Referring again to FIG. 5A, laser system 501, displacement meter 502, and hardware 507 are communicatively coupled to control computer 504 (e.g., through RS-232C or USB cables, WiFi or BLUETOOTH™ wireless functionality, etc.). Control computer 504 may include conventional computer components such as a processor, memory, input/output interfaces and ports, a keyboard, a display, input peripheral(s), etc. (not individually depicted in FIG. 5A). Control computer 504 also includes executable software stored within memory of computer 504. The software communicates with laser system 501 and displacement meter 502 to control the operations of system 500 (e.g., through one or more application programming interfaces (APIs)). For example, the software may control displacement meter 502 to scan sheath 405. The software may control laser system 501 to apply laser pulses at specific positions along sheath 405 to create the desired apertures in the outer surface of sheath 405 to respective lumens within sheath 405. The software may include software distributed by the vendors of laser system 501 and sheath 405.

The software may also include special-purpose software to process the data from displacement meter 502 to select positions for application of laser pulses on sheath 405. The special purpose software may also include interface software 506 for presenting a generated profile of the sheath cross-section. Software 506 may also display the automatically selected locations along the sheath for application of laser pulses for review by the operator of system 500. Respective segments of software code are preferably implemented or provided to receive data from an appropriate source (e.g., representing sheath data or system data), process the data, and communicating control signals to implement each respective functional task discussed herein.

In operation, control computer 504 initially causes displacement meter 502 in conjunction with rotation hardware 507 to scan across the circumference of sheath 405 at one or more respective axial locations along sheath 405. The functionality of displacement meter 502 is known and is briefly described herein. Displacement meter 502 generates a laser beam and applies the beam to sheath 405 through an objective lens. The lens is vibrated up and down at a relatively high speed (e.g., by a tuning fork). The beam is reflected by the insulative material of sheath 405 and is converged on a pinhole. The light re-enters the light-receiving element of meter 502. By measuring the exact position of the lens when the light enters the light-receiving element, the displacement distance is calculated. Using this data, a detailed "end-view" profile can be plotted and displayed.

In one embodiment, the insulative material of sheath 405 is Elast-Eon® polymer material (a silicone-polyurethane co-polymer insulation developed by AorTech International Plc). This material and other similar implantable materials are transparent. Since the insulative material of sheath 405 is transparent, peak values of light are produced by respective layers within sheath 405 (e.g., where the insulative material of sheath 405 transitions to the empty space defined by a lumen). However, resolution of the internal characteristics of sheath 405 is complicated by the internal reflections within sheath 405 caused by the respective lumens. Some embodiments, implemented within control computer 504 and processing software 505, apply suitable processing algorithms (implemented within displacement meter data processing software 505) to resolve the displacement data into a data representation of the cross-sectional profile of sheath 405.

Using the generated cross-sectional profile, processing software 505 also automatically identifies the respective lumens, determines distances from the lumens to the surface of sheath 405, and identifies a respective location on the surface of sheath 405 for application of one or more laser pulses to create the desired window (if appropriate). In some embodiments, the locations are selected for all of the lumens of sheath 405. In other embodiments, the locations are selected only for a lesser subset of lumens. For example, in one embodiment, locations are only selected for the three smaller lumens of sheath 405. In some embodiments, the angular locations for application of a laser pulse may be selected at locations where the distance between a respective lumen and the outer surface of the sheath is smallest. The axial location are selected according to the electrode/sensor configuration of the lead design.

Some representative embodiments are adapted to address variations in the sheath characteristics. For example, the distance from the surface of sheath 405 to each respective lumen may vary due to variations in the manufacturing process used for sheath 405. If the distance is too small, it is possible that the creation of a window to access the respective lumen may cause failure of the sheath 405 (e.g., permit entry of bodily fluids within a given lumen after implantation within a patient). Some representative embodiments automatically calculate the distance from the outer surface of sheath 405 to the lumen. If the distance is too small (e.g, as defined by a constraint in software), control software on control computer 504 will attempt to identify another axial location along sheath 405 that is suitable for the respective electrode or sensor and where the distance is sufficient. Excess length may be provided to an initial segment of sheath 405 beyond the length necessary for fabrication of a suitable lead to accommodate for this contingency.

Figure 6:
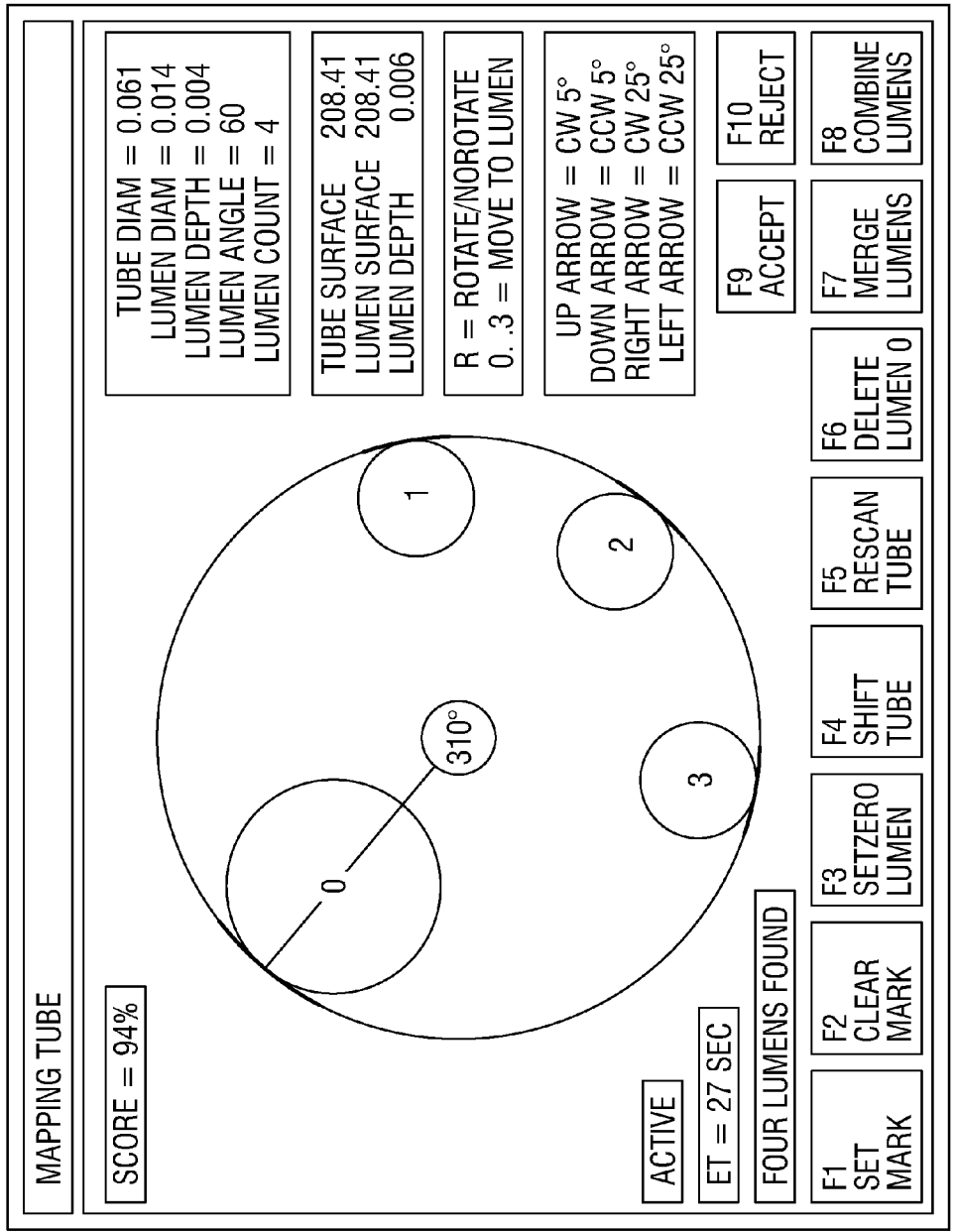
FIG. 6 depicts an interface screen for controlling the system shown in FIG. 5A according some representative embodiments.

FIG. 6 depicts display screen 600 for generation by interface software 506. Display screen 600 presents a graphical representation of the cross-section of sheath 405 after scanning and analysis by software 505. Selected data (as generated or calculated by software 505) may be presented to the operator of system 500 including the diameter of sheath 405, lumen diameter information, lumen angle, and lumen depth (e.g., distance from the sheath surface), etc. Display screen 600 may display an automatically calculated location for application of laser pulses by one or more lumens. The operator may review the presented information. If appropriate, the user may accept the presented information to permit laser operations to occur. In some embodiments, the user may manually modify the locations. Additionally or alternatively, the operator may initiate a rescan at a different axial position (if deemed appropriate by the operator).

Figure 7:
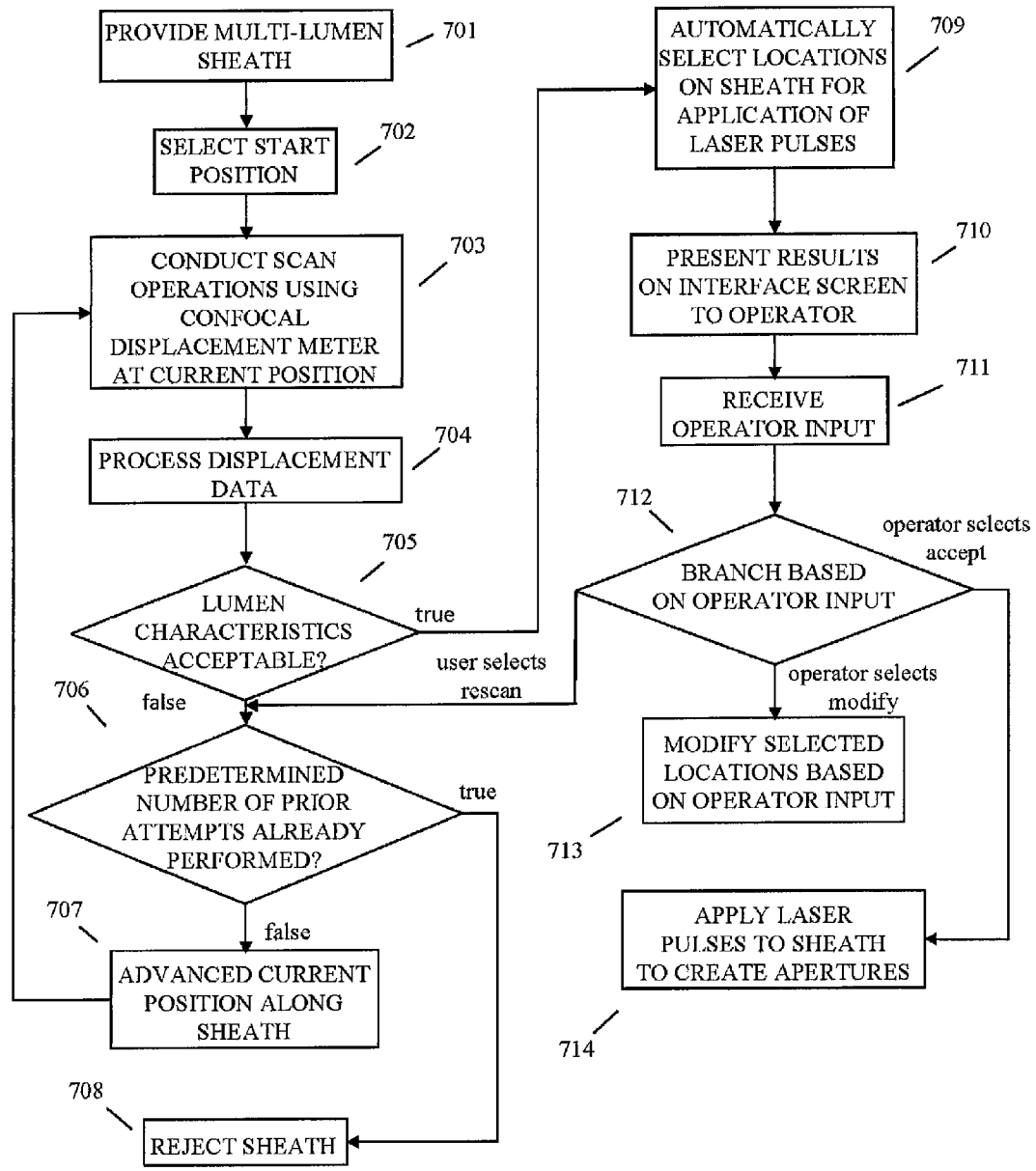
FIG. 7 depicts a flowchart for creating apertures or holes in a sheath during fabrication of an implantable lead according to some representative embodiments.

FIG. 7 depicts a flowchart of operations for creating apertures in a sheath for use in fabricating an implantable lead. In 701, a multi-lumen sheath (e.g., multi-lumen sheath 405) is provided to a suitable micromachining system. The sheath is placed within lead manipulation hardware for translation and rotation during various operations. In 702, a start position for the sheath is selected (e.g., a particular axial location near the distal end of the sheath).

In 703, scan operations using a confocal displacement meter device are performed for one or more locations on the sheath. The location(s) may be selected relative to the current position and the intended electrode/sensor configuration for the lead design. Axial translation and rotation of the sheath may be applied by the system between the respective scan operations.

In 704, the data from the displacement meter for scan position(s) is processed. The processing may include generating a cross-sectional profile of the sheath at the various scan locations. Also, the processing may include identifying the outer diameter of the sheath, identifying lumens (including lumen diameter and lumen position), and identifying the distance from the lumens to the outer surface of the sheath.

In 705, a logical comparison is made to determine whether the lumen data indicates that the lumen characteristics are acceptable at the respective locations (e.g., whether the lumens are within an acceptable distance from the outer surface of the sheath). If not, the process flow proceeds to step 706.

If a predetermined number of attempts have not been made (see logical comparison at 706), the current position is advanced by a predetermined distance axially along the sheath (707) and the process returns to step 703 to repeat the scanning processing at the new location. If the predetermined number of attempts have already been made, the process flow ends by rejecting the sheath before further processing occurs (708).

In 709, locations about the sheath are automatically selected for application of laser pulses to create the intended apertures. The angular component of locations about the circumference of the sheath are selected using the calculated lumen positions. Also, the axial locations along the length of the sheath are selected according to the intended electrode/sensor positions for the lead design.

In 710, the calculated results are presented to the operator of the system using an interface screen on a display of the system. The interface screen may include a cross-sectional representation of the sheath. The calculated sheath diameter and lumen data may be displayed. The interface screen is preferably adapted to receive user input to control further operations. As shown in the flowchart, in 711, operator input is received. In 712, a logical comparison is made based on the operator input. In one case, rescan operations may be attempted (e.g., at a new location). In another case, one or more of the automatically selected locations are modified according to additional user input (713) for subsequent laser operations. Also, if the automatically selected locations are accepted by the operator, the process flow may proceed immediately.

In 714, laser operations are performed to create the desired apertures for access to the respective lumens of the sheath at the automatically selected locations (or as modified by the operator). The laser operations may include rotation and/or axial translation of the sheath to place each desired location within the field of the laser pulses. Beam control and motion control operations of the laser device may also be controlled to ensure that the laser pulses are applied to selected locations. After creation of the apertures, the sheath is ready for further processing to create an implantable lead.

An implantable lead may be fabricated from the processed sheaths with the provided apertures or holes. Conventional (or subsequently developed) processes may be applied to fabricate the implantable leads from the processed sheaths. For example, conductor wires, cables, or coils may be introduced through the respective lumens. A welding element (a "slug") may be attached to the respective coils or cables. The welding elements on the coils or cables may be advanced through the respective lumens until the welding elements are adjacent to the apertures or holes. Electrodes and/or sensors are provided. The electrodes and sensors are electrically coupled to the welding elements (e.g., using laser weld operations), possibly using intermediate conductive elements. Crimping, swaging, or any other suitable technique may be employed for securing the electrodes/sensors about the sheath.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of fabricating an implantable lead for providing electrical pulses to tissue of a patient, the method comprising:
   (i) providing a sheath of transparent insulative material, wherein the sheath comprises a plurality of lumens;
   (ii) scanning across the sheath with a confocal displacement meter to generate displacement data;
   (iii) processing the displacement data, in software executed on a computer system, to generate a representation of an exterior surface and lumens of the sheath;
   (iv) automatically selecting locations, in software executed on a computer system, on the exterior surface for application of laser pulses to create apertures in the sheath that provide access to respective lumens of the sheath, wherein the automatically selecting locations comprises automatically calculating, by software executed on a computer system, distances from lumens of the sheath to the exterior surface of the sheath and determining whether the calculated distances from the lumens to the exterior surface satisfy a defined constraint by software executed on the computer system, wherein steps (i)-(iv) are repeated for another axial location along the sheath before proceeding to (v) in response to determining that the calculated distances do not satisfy the defined constraint; and
   (v) applying laser pulses to the sheath to create the apertures.

2. The method of claim 1 wherein the transparent insulative material is a silicone-polyurethane co-polymer insulation.

3. The method of claim 1 wherein (i) the sheath comprises a generally central lumen and three lumens along a periphery of the sheath and wherein (ii) the automatically selecting locations selects locations on the exterior sheath adjacent to the three lumens along the periphery of the sheath.

4. The method of claim 1 further comprising:
providing an interface screen, by software executed on a computer system, for presentation to an operator that provides a cross-sectional representation of the sheath.

5. The method of claim 1 further comprising:
receiving input from the operator via the interface screen to accept the automatically selected locations before proceeding to (v).

6. The method of claim 5 further comprising:
receiving input from the operator via the interface screen to modify one or more of the automatically selected locations according to operator input before proceeding to (v).

7. The method of claim 1 further comprising:
communicating commands, by software executed on a computer system, for sheath translation hardware to translate the sheath from a position to be scanned by the displacement meter to a position to receive laser pulses.

8. A system for processing a multi-lumen sheath suitable for a medical lead for application of electrical pulses to tissue of a patient, the system comprising:
a confocal displacement meter;
a micro-machining laser system including a laser source and motion control components;
a processor for controlling the system according to software instructions; and
memory for storing data and software instructions, wherein the memory stores (a) code for causing the system to scan the multi-lumen sheath to generate displacement data; (b) code for processing the displacement data to generate a representation of an exterior surface and lumens of the multi-lumen sheath; (c) code for automatically selecting locations on the exterior surface of the multi-lumen sheath for application of laser pulses to create apertures in the multi-lumen sheath that provide access to respective lumens of the multi-lumen sheath, wherein the code for automatically selecting comprises (i) code for automatically calculating distances from lumens of the multi-lumen sheath to the exterior surface of the multi-lumen sheath; (ii) code for determining whether the calculated distances from the lumens to the exterior surface satisfy a defined constraint; and (iii) code for repeating execution of the code for causing the system to scan, code for processing the displacement data, and code for automatically selecting for another axial location along the sheath in response to determining that the calculated distances do not satisfy the defined constraint; and (d) code for applying laser pulses to the sheath to create the apertures.

9. The system of claim 8 wherein (i) the multi-lumen sheath comprises a generally central lumen and three lumens along a periphery of the sheath and wherein (ii) the code for automatically selecting locations selects locations on the exterior sheath adjacent to the three lumens along the periphery of the sheath.

10. The system of claim 8 wherein the memory further stores code for providing an interface screen for presentation to an operator that provides a cross-sectional representation of the multi-lumen sheath.

11. The system of claim 10 wherein the memory further stores code for receiving input from the operator via the interface screen to accept the automatically selected locations before execution of the code for applying laser pulses.

12. The system of claim 11 wherein the memory further stores code for receiving input from the operator via the interface screen to modify one or more of the automatically selected locations before execution of the code for applying laser pulses.

* * * * *